United States Patent
Palya

(10) Patent No.: US 11,607,527 B2
(45) Date of Patent: Mar. 21, 2023

(54) APPARATUS AND METHODS FOR SECURING MEDICAL TUBES ON PATIENTS

(71) Applicant: Gus Gear, Inc., Valencia, PA (US)

(72) Inventor: Sarah Palya, Valencia, PA (US)

(73) Assignee: Gus Gear, Inc., Valencia, PA (US)

(*) Notice: Subject to any disclaimer, the term of this patent is extended or adjusted under 35 U.S.C. 154(b) by 0 days.

(21) Appl. No.: 16/680,872

(22) Filed: Nov. 12, 2019

(65) Prior Publication Data

US 2021/0138199 A1    May 13, 2021

(51) Int. Cl.
*A61M 25/02* (2006.01)

(52) U.S. Cl.
CPC ..... *A61M 25/02* (2013.01); *A61M 2025/0206* (2013.01); *A61M 2025/0213* (2013.01)

(58) Field of Classification Search
CPC .. A61M 2025/0206; A61M 2025/0213; A61M 25/02; A61M 2025/0253; A61M 2025/026
See application file for complete search history.

(56) References Cited

U.S. PATENT DOCUMENTS

| | | | |
|---|---|---|---|
| 5,755,698 A * | 5/1998 | Kagan | A61M 25/02 604/179 |
| 5,941,856 A | 8/1999 | Kovacs et al. | |
| 6,032,289 A * | 3/2000 | Villapiano | A41D 13/1245 2/102 |
| 6,206,854 B1 | 3/2001 | Weaver | |
| 6,540,724 B1 | 4/2003 | Harris | |
| 7,201,739 B2 | 4/2007 | Walborn | |
| D756,510 S | 5/2016 | Fitzgerald et al. | |
| D761,419 S | 7/2016 | Fitzgerald et al. | |
| 9,526,870 B2 | 12/2016 | Simons et al. | |
| 2005/0020977 A1 * | 1/2005 | Eldridge | A61M 25/02 604/111 |
| 2005/0033241 A1 | 2/2005 | Hottinger | |

(Continued)

FOREIGN PATENT DOCUMENTS

CN    204446920 U    7/2015

OTHER PUBLICATIONS

Palya, Sarah, Gus Gear Central Line Wraps, marketing materials publicly available in 2018.
PCT/ISA/210—International Search Report dated Feb. 4, 2021.

*Primary Examiner* — Amber R Stiles
(74) *Attorney, Agent, or Firm* — Metz Lewis Brodman Must O'Keefe LLC

(57) ABSTRACT

Securing a medical tube in fluid communication with the interior of a patient is accomplished with an apparatus having a support portion with a mounting surface thereon, a cover portion for the mounting surface that releasably attaches to the mounting surface to define an inner chamber, and a plurality of fingers to define at least one access slit for a medical tube to pass through. The assembly also has a detachable fastener element for securing the medical tube in the assembly. The plurality of fingers releasably connect to one another to define at least one access slit with the medical tube extending through the access slit. The plurality of fingers can be disconnected from one another to open the access slit, thereby facilitating removal of the substrate from the patient without disturbing the fluid communication between the medical tube and interior of the patient.

17 Claims, 6 Drawing Sheets

(56) References Cited

U.S. PATENT DOCUMENTS

| | | | |
|---|---|---|---|
| 2009/0054844 A1* | 2/2009 | Alyea | A41D 13/1245 604/179 |
| 2009/0139061 A1 | 6/2009 | Nishtala | |
| 2009/0216197 A1 | 8/2009 | Russo | |
| 2009/0254040 A1 | 10/2009 | Bierman et al. | |
| 2010/0137805 A1* | 6/2010 | Farchione | A61M 25/02 604/179 |
| 2011/0023208 A1* | 2/2011 | Liao | A61M 25/02 2/102 |
| 2013/0023827 A1 | 1/2013 | Nokes, Jr. et al. | |
| 2014/0188079 A1 | 7/2014 | Simons et al. | |
| 2014/0237697 A1 | 8/2014 | Corado | |
| 2016/0050995 A1 | 2/2016 | Bentley et al. | |
| 2017/0136215 A1* | 5/2017 | Harders | A61M 25/02 |

* cited by examiner

APPARATUS AND METHODS FOR SECURING MEDICAL TUBES ON PATIENTS

FIELD OF THE INVENTION

The present disclosure relates to apparatus and methods for securing medical tubes in patients. More particularly, the invention is directed to a wearable apparatus that has at least one enclosed, detachable fastener element for securing a medical tube.

BACKGROUND OF THE INVENTION

Medical tubes include certain medical devices, such as central lines, feeding tubes, catheters, and other similar devices. One particular class of medical tubes, central venous access devices (CVADs), can be used to deliver medications, hydration, and intravenous feeding. CVADs can be used in the treatment of such conditions as cancer, short gut syndrome, chronic intestinal pseudo obstruction, Crohn's disease, ulcerative colitis, mitochondrial disease, cystic fibrosis, and many others.

Tunneled central lines are thin catheters inserted under the skin and into a large vein for long-term use and are particularly fragile in several locations including the thinnest part of the line and near the hub. Line repair is reported in as many as 33% of catheters and there is a 3-fold increase in the occurrence of sepsis in the thirty days following line repair.

Certain medical tubes present particularly difficult problems when used with children due to their lack of safety awareness, nearly constant movement, and poor impulse control. Children who are infusing via central lines sometimes need to infuse continuously for the delivery of food and medicine. These children often forget the tubing needs to stay in place and may tug on the tubing, which can break a fragile central line or cause the line to be dislodged, thus exposing the line to contamination and infection. Indeed, some children have severed the line completely, which can result in a life-threatening event.

Line trauma is a common cause for repair in pediatric applications. Currently, pediatric tunneled CVADs have a failure rate of 29% prior to completion of therapy. This leads to a significant burden on the healthcare system by necessitating additional time in the hospital to place a new line, lost time receiving treatment or nutrition, loss of access site (only six available vessels), and the potential for further complications including death. Preventing line trauma directly impacts long-term outcomes by preserving central access, with clinicians seeking a safe CVAD device to minimize line trauma and its resulting complications.

Another type of medical device, medical wraps, can be used with medical tubes. Medical wraps or wrappings are employed to wrap about portions of the human or animal body for medical treatment. Well-known examples include elongated bandages; however, some medical wraps provide functions in addition to serving as bindings. For example, some wraps structurally support and stabilize broken or sprained limbs and joints. Others are employed to hold hot packs or cold packs up against the skin. In some instances, medical wraps have been employed to secure medical tubes to patients.

Unfortunately, conventional medical wraps are not particularly effective at keeping central lines safe, secure, and free from being pulled from the patient. Conventional medical wraps are not particularly effective at limiting the risk of line breakage. Moreover, such devices are not designed to provide accessibility to the central line. Accordingly, there is a need for an improved medical tube securing device.

SUMMARY OF THE INVENTION

The following summary is provided to introduce a selection of concepts in a simplified form that are further described below in the detailed description. This summary is not intended to identify key features or essential features of the claimed subject matter, nor is it intended to be used to limit the scope of the claimed subject matter.

Securing a medical tube assembly having a medical tube in fluid communication with the interior of a patient at an insertion point is accomplished with a substrate having a support portion with a mounting surface thereon, a cover for the mounting surface that releasably attaches to the substrate to define an inner chamber, and a plurality of fingers to define at least one access slit with the medical tube extending through the access slit. A detachable fastener element having a tube holder for securing the medical tube assembly and a mounting member abutting the substrate support mounting surface to releasably connect the fastener element to the substrate support mounting surface. The fastener element tube holder aligns at least a portion of the medical tube assembly in fixed relation to the substrate support mounting surface within the inner chamber. The plurality of fingers releasably connect to one another to define at least one access slit with the medical tube extending through the access slit. The plurality of fingers can be disconnected from one another to open the access slit, thereby facilitating removal of the substrate from the patient without disturbing the fluid communication between the medical tube and interior of the patient.

These and other features and advantages will be apparent from a reading of the following detailed description and a review of the appended drawings. It is to be understood that the foregoing summary, the following detailed description and the appended drawings are explanatory only and are not restrictive of various aspects as claimed.

BRIEF DESCRIPTION OF THE DRAWINGS

For a fuller understanding of the nature and advantages of the present invention, reference should be made to the following detailed description, taken in connection with the accompanying drawings, in which.

DETAILED DESCRIPTION OF THE DRAWINGS

Figure 1:
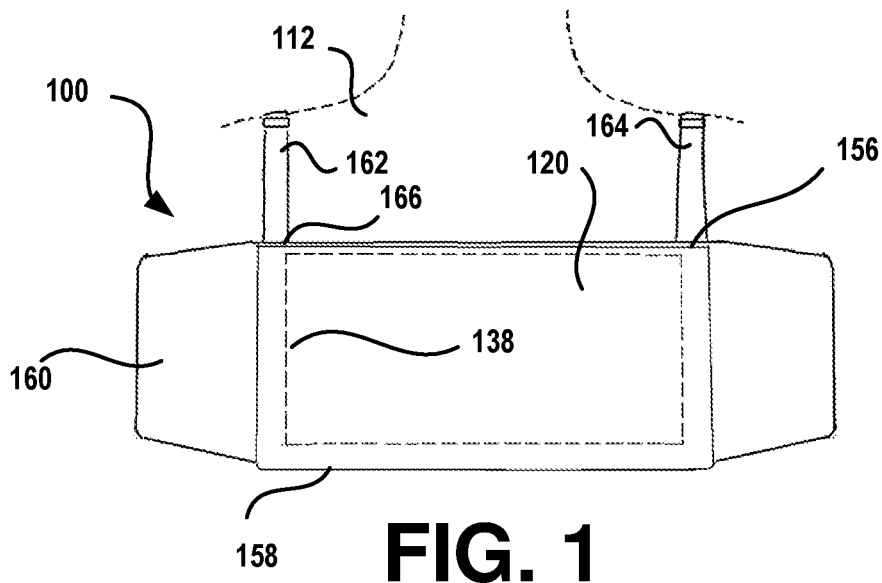
FIG. 1 is a front view of a closed apparatus for securing a medical tube in accordance with this disclosure.

The detailed description provided below in connection with the appended drawings is intended as a description of examples and is not intended to represent the only forms in which the present examples can be constructed or utilized. The description sets forth functions of the examples and sequences of steps for constructing and operating the examples. However, the same or equivalent functions and sequences can be accomplished by different examples.

References to "one embodiment," "an embodiment," "an example embodiment," "one implementation," "an implementation," "one example," "an example" and the like, indicate that the described embodiment, implementation or example can include a particular feature, structure or characteristic, but every embodiment, implementation or example can not necessarily include the particular feature, structure or characteristic. Moreover, such phrases are not necessarily referring to the same embodiment, implementation or example. Further, when a particular feature, structure or characteristic is described in connection with an embodiment, implementation or example, it is to be appreciated that such feature, structure or characteristic can be implemented in connection with other embodiments, implementations or examples whether or not explicitly described.

The term "patient" and "subject" are interchangeable and can be taken to mean any living organism. As such, the terms "patient" and "subject" can include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "surface fasteners" can refer to fasteners such as hook and loop fasteners in which molded hook elements, such as single hook shapes, mushroom shapes, palm tree shapes or other shapes, releasably engage in loop elements as provided by low-cost non-woven or light-weight knit materials. Some surface fasteners are sold under the name VELCRO®, which is a registered trademark of Velcro Industries B.V. of Willemstad, Cura şcao.

The term "surface fasteners" can also refer to so-called "self-engaging" fasteners that have fastener elements of one or more kinds that engage with like fasteners on another surface and to fastener surfaces of materials that are adhesive or cohesive or otherwise engage with one another by action of overlying surfaces.

Numerous specific details are set forth in order to provide a thorough understanding of one or more aspects of the described subject matter. It is to be appreciated, however, that such aspects can be practiced without these specific details. While certain components are shown in block diagram form to describe one or more aspects, it is to be understood that functionality performed by a single component can be performed by multiple components. Similarly, a single component can be configured to perform functionality described as being performed by multiple components.

The disclosed invention is directed to a wearable apparatus that is particularly adapted for securing medical tubes and, in particular, central lines. The wearable apparatus can be made from washable, flexible material that can wrap around the torso of a patient. Notably, the wearable apparatus can also be constructed of a disposable material. The wrap can cover an exit site, a dressing, and at least a portion of the line itself. The apparatus can include one or more adjustable straps and can be adjustable around the torso to allow for growth.

The wrap can keep medical tubes safe and secure, while dramatically lessening the risk of accidental pullout and line breakage. The wrap can be used while infusing and when disconnected. The wrap can include a front flap that provides security and easy accessibility. The sturdy construction of the wrap can absorb energy from line pulls, resulting in an undamaged central line.

The wrap utilizes a plurality of fingers that can be releasably connected to one another. The fingers define one or more access slits that surround a central line or other medical tube when a patient wears the wrap. The fingers can be released to open or spread the access slit apart to facilitate installation or removal of the wrap from the patient without disturbing the central line or medical tube or exposing the central line or medical tube to contamination. Removal of the wrap in this manner provides for easy cleaning.

Referring to FIGS. 1-7, an apparatus, generally designated with the numeral 100, is shown in various stages of assembly for purposes of clarity. In certain embodiments, the apparatus 100 is particularly adapted for securing a medical tube assembly 110 against the body 112 of a patient. The apparatus 100 includes a substrate 114 and at least one detachable fastener element 116. The substrate 114 includes a support portion 118 and a cover portion 120. The medical tube assembly 110 includes a medical tube 122 and a connector 124.

In embodiments, the apparatus 100 can be a central line wrap that secures a central catheter and prevents line pulls from damaging the catheter. In some embodiments, the apparatus 100 can absorb energy from line pulls which can result in an undamaged central line. In some embodiments, the central line wrap can protect a tunneled central catheter and prevents line trauma in a subject.

Additionally, the apparatus 100 can reduce the frequency, severity, or a combination thereof of medical adhesive related skin injury (MARSI). In some embodiments, the apparatus 100 can reduce the frequency, severity, or a combination thereof of dislodgement of many types of lines and tubes including, for example, catheter lines, trachea tubes, intravenous catheters, ports, PICC lines, and others. In some embodiments, the apparatus 100 can reduce the frequency, severity, or a combination thereof of catheter line damage or trachea tube damage. In some embodiments, the apparatus 100 can reduce the frequency, severity, or a combination thereof of catheter pistoning (e.g. moving back and forth in the vein). In further embodiments, the apparatus 100 can reduce the frequency, severity, or a combination thereof of catheter-related bloodstream infection. In some embodiments, the apparatus 100 can reduce the frequency, severity, or a combination thereof of torsion. In some embodiments, the apparatus 100 can protect the entire catheter line.

The support portion 118 includes a mounting surface 126 with sufficient area to accommodate the attachment of a first fastener element 116 and a second fastener element 128. The cover portion 120 can connect, at least partially, to the support portion 118 along a plurality of seams 130-136 to enclose the mounting surface 126 and the fastener elements 116 and 128, as shown in FIG. 1. In such a configuration, the support portion 118 and the cover portion 120 cooperate to define an inner chamber or pouch 138 (shown in phantom in FIG. 1) for holding and protecting the fastener elements 116, 128, and the medical tube assembly 110 therein. In certain embodiments, only a single fastener may be used, such as if the single fastener had multiple locations for holding a medical tube in a desired location and orientation.

The cover portion 120 can be releasably attached to the support portion 118 along at least one of the plurality of seams 130, 134, and 136 with one or more bonding strips 140-144 to envelop the fastener elements 116, 128, and the medical tube assembly 110 in the inner chamber 138. In certain embodiments, the cover portion 120 is integral with the support portion 118 at seam 132. The cover portion 120 releasably connects to the support portion 118 with surface fasteners along the other seams 130, 134, and 136.

The substrate 114 can have bonded seams, stitched seams, or a combination thereof. In some embodiments, the substrate 114 having bonded seams provides stability to the apparatus 100. In some embodiments, the substrate 114 having stitched seams provides stability to the apparatus 100. In some embodiments, the substrate can be made from a bonded material, having bonded seams, or a combination thereof can reduce the stitching and doubled seams in the substrate 114.

In some embodiments, the substrate 114 can have one or more vertical stitched seams. In some embodiments, the one or more vertical stitched seams provides strength, durability, or a combination thereof to the substrate 114. In some embodiments, the one or more vertical stitched seams prevents damage to the substrate 114.

The cover portion 120 can be disconnected from the support portion 118 to allow the fastener elements 116, 128, and the medical tube assembly 110 to be removed from the inner chamber 138, which is one of the advantages of the apparatus 110 over conventional wraps. The ability to remove the fastener elements 116, 128, and the medical tube assembly 110, as will be more fully explained, facilitates the washing and/or cleaning of the substrate 114 and eliminates the need to disconnect the medical tube 122 from the body 112 to remove the apparatus 100.

Figure 5:
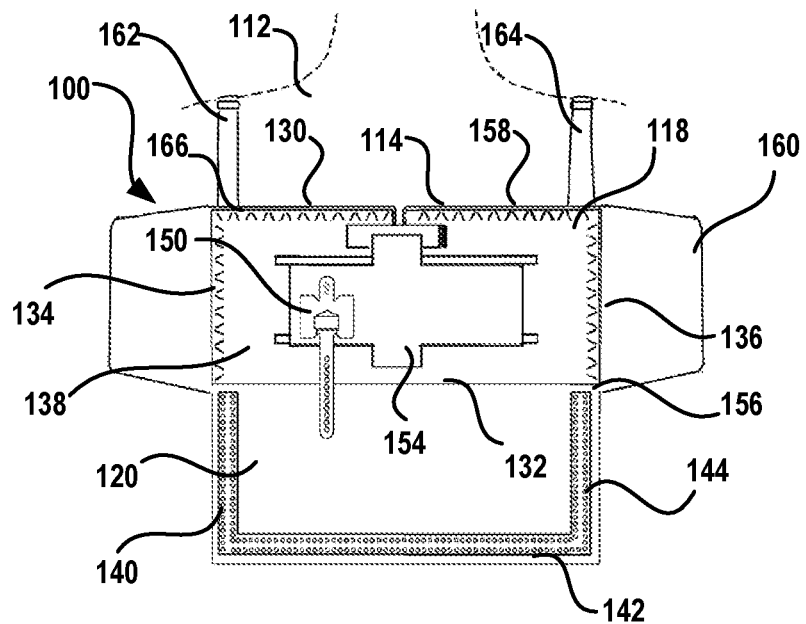
FIG. 5 is another front view of the partially assembled apparatus shown in FIG. 1 illustrating a detachable fastener element releasably attached to the substantially planar mounting sheet.
Figure 6:
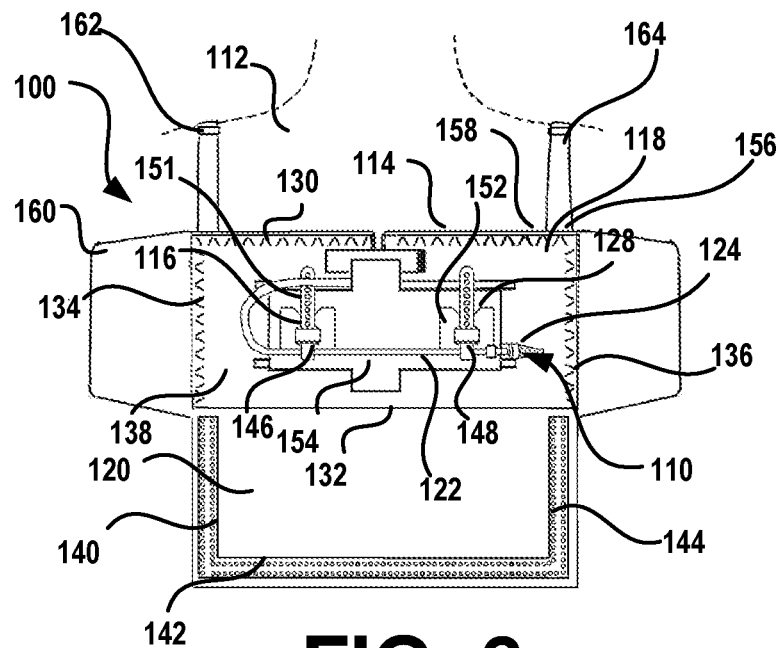
FIG. 6 is a fragmentary front view of the partially assembled apparatus shown in FIG. 1 illustrating a plurality of detachable fastener elements releasably attached thereon.

As shown in FIGS. 5-6, the fastener elements 116 and 128 can include strap receivers 146-148 and straps 151 that coordinate with the strap receivers 146-148 to create loops of varying sizes depending on the size of the particular medical tube 122 being secured. The fastener elements 116, 128 encircle the medical tubes 122 to secure them to the support portion 114 of the substrate 118. The strap receivers 146-148 have bases 150-152 that are attached to the support portion 118 of the substrate 114. In certain embodiments, a stability sheet 154 is added between the fastener elements 116, 128 and the support portion 118 to provide added stability for the fastener elements 116, 128. In most embodiments, the strap receivers 146-148 coordinate with the straps to form loops for receiving and holding medical tubes, such as medical tube 122 shown in FIGS. 5-7, therein.

In embodiments, the bases 150-152 can be attached (releasably or otherwise) to the stability sheet 154 with the stability sheet 154 being releasably attached to the support portion 118 in the area of the fingers to provide additional support thereto. In such embodiments, the stability sheet 154 supports the fastener elements 116 and 128. In other embodiments, the bases 150-152 can be releasably connected to the support portion 118 directly.

In certain embodiments, as is further illustrated in FIG. 6, the straps 151 are oriented in an essentially perpendicular direction from an axis of seam 132. The fastener elements 116, 128 hold the medical tube assembly 110 with portions of the medical tube 122 being held in fixed relation to the mounting surface 126. In some embodiments, a central axis of a portion of the medical tube 122 is aligned substantially parallel to the support portion 118 within the inner chamber 138 when the cover portion 120 is attached to the support portion 118.

As shown in FIGS. 1-7, the substrate 114 can form an enclosure 156 designed to be worn about the body 112. The enclosure 156 can include a substantially flat thicker mounting section 158. A thinner extending connecting section 160 is attached to left and right sides of the enclosure 156 and encircles the body 112 in certain embodiments.

The mounting section 158 includes the support portion 118 and the cover portion 120. A plurality of shoulder straps 162-164 can assist with holding the enclosure 156 in place. In various embodiments, the straps 162-164 can be attached to an outer edge 166 of the substrate 114. In some embodiments, the straps 162-164 connect to the mounting section 158 and the connecting section 160.

Additionally, the enclosure 156 can be made from a plurality of materials, including elastic materials, polymers, plastics, or combinations thereof. The materials can be lightweight materials, flexible materials, elastic materials, bonded materials, and/or a combination thereof. In some embodiments, the material can be a breathable fabric, a cotton material, a synthetic hybrid material, a charged cotton fabric, an absorbent material, a material designed to wick and spread moisture away from the skin, or combinations thereof. In some embodiments, the materials can be disposable.

In some embodiments, the enclosure 156 can be made from a first material, a second material, and a poly cotton material. Suitable materials can include a first nylon supplex fabric, a second nylon supplex fabric, and a polycotton material wherein the poly cotton material is layered between the first and the second nylon supplex fabric. The materials can include a first nylon supplex fabric, a second nylon supplex fabric, and an adhesive film or tape wherein the adhesive film or tape is layered between the first and the second nylon supplex fabric, and wherein addition of heat provides a bonded body structure. Other suitable materials include a first nylon supplex fabric, a second nylon supplex fabric, and a Bemis adhesive film or tape wherein the Bemis adhesive film or tape is layered between the first and the second nylon supplex fabric, and wherein addition of heat provides a bonded body.

The material can be selected for patient comfort and for ease of removal. The body can be hand washable or machine washable to ensure that the enclosure 156 can be removed and cleaned rapidly, when necessary. In some embodiments, the mounting section 158 and the connecting section 160 are integral that can include one material or a combination of materials. In other embodiments, the mounting section 158 and the connecting section 160 can be made from separate components that can include one material or a combination of materials.

The enclosure 156 can be made from a material that is non-invasive, non-adhesive, or a combination thereof. In further embodiments, the material can reduce medical adhesive related skin injuries (MARSI).

Figure 2:
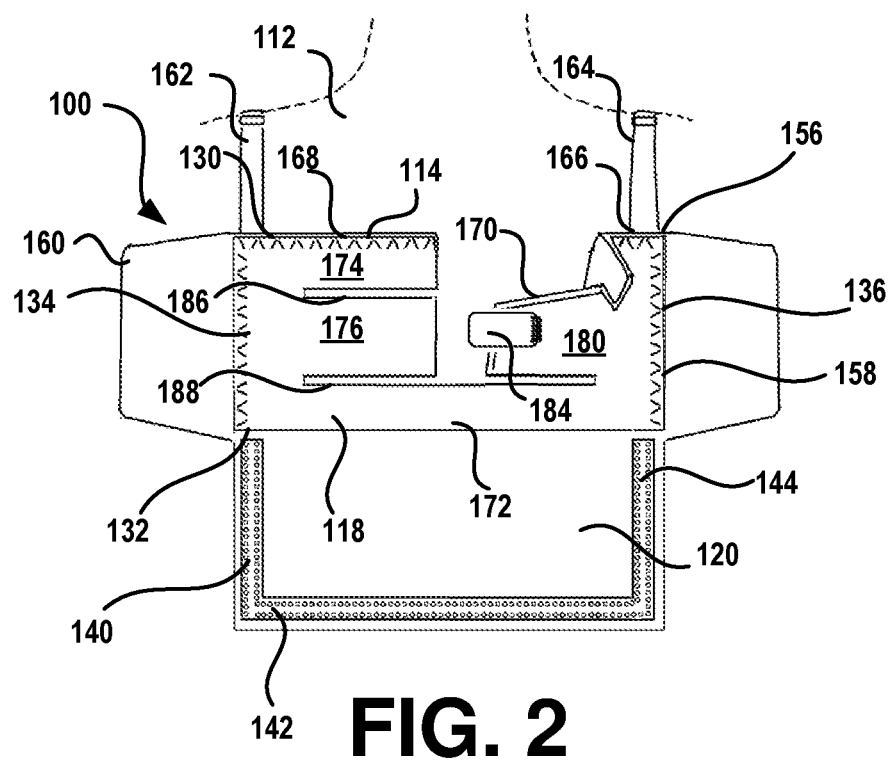
FIG. 2 is a front view of the partially assembled apparatus shown in FIG. 1 in an open position.
Figure 3:
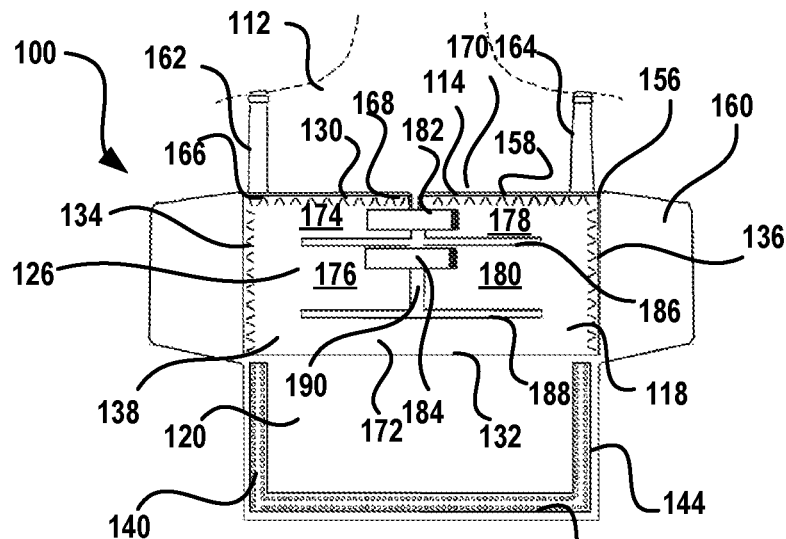
FIG. 3 is another front view of the partially assembled apparatus shown in FIG. 1 in an open position.
Figure 4:
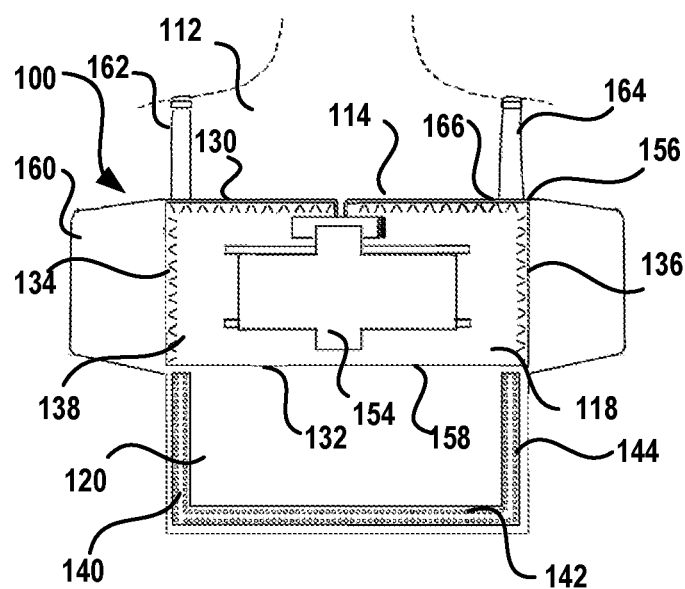
FIG. 4 is another front view of the partially assembled apparatus shown in FIG. 1 illustrating a substantially planar mounting sheet releasably attached to a substrate.

Referring now to FIGS. 2-3 with continuing reference to foregoing figures, the support portion 118 can be a substantially flat flexible sheet that can be divided into two flap portions 168-170 and a lower band 172 that connects to the connecting section 160 at the seams 134-136 to form a back portion of the enclosure 156. Each of the flap portions 168-170 are divided into two or more fingers 174-180 that are formed from the substrate 114 and can be folded away from the body 112 as demonstrated in FIG. 2. In embodiments, the flap portions 168, 170 are mirror images of each other. Put another way, each finger 174-180 can be pulled away from an imaginary vertical line whereby medical lines can be fed through the support portion 118.

One or more fastener strips 182-184 connects opposing fingers 174, 178 and 176, 180 to one another. In embodiments, fastener strips 182-184 are attached to one of the opposing fingers and not the other. For example, fastener strips may be permanently affixed to fingers 174 and 176 through conventional connection means but not to 178 and 180. The fastener strips 182-184 releasably attach to the opposing fingers 178-180 using surface fasteners or other removable fasteners known in the art. In alternative embodiments, the fasteners are releasably attached to both pairs of fingers 174-180.

The fingers 174-180 can releasably connect to one another to define one or more access slits 186-190 that receive medical tubes, such as medical tube 122 shown in FIG. 6. When the fingers 174-180 are connected to one another, the access slits 186-190 are closed to hold the medical tubes in place.

Figure 7:
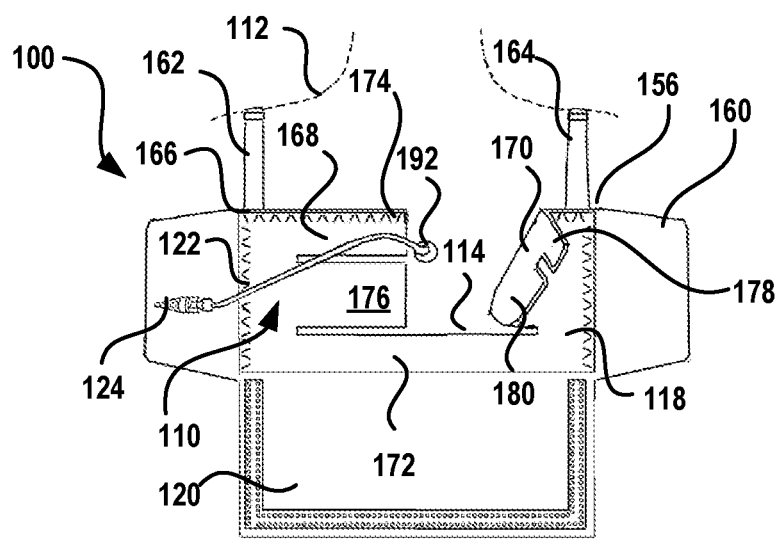
FIG. 7 is a front view of the partially disassembled apparatus shown in FIG. 1.

As illustrated in FIG. 7, when the fingers 174-180 are separated from one another, the medical tube 122 is released from the slits and, as long as the fastener elements 116, 128 have been disconnected, the apparatus 100 can be removed from the body 112 of a patient without disturbing the fluid communication between the medical tube 122 and the interior of the patient.

In some embodiments, the fastener strips 182-184 are strips having surface fasteners thereon. In other embodiments, the fastener strips 182-184 can be buckles, clips, hooks, or clasps. The fastener strips 182-184 can be similar to hook and loop-type detachable bra strap fasteners.

In embodiments, the lower band 172 and the fingers 174-180 form a plurality of slits 186-190. The medical tube 122 can be inserted through the slits 186-190, so that the flap portions 168-170 can surround a portion of the medical tube 122 that extends through the substrate support portion 118. In some embodiments, the fingers 174-180 represent means for receiving the medical tube 122 therein. In other embodiments, the lower band 172 in combination with the fingers 174 represent means for receiving the medical tube 122 therein.

Referring to FIG. 7 with continuing reference to the foregoing figures, the apparatus 100 can be disassembled without disturbing the medical tube 122 at the point of insertion 192 (i.e., the patient's exit site) into the patient 112. After the fastener elements 116, 128 have been disconnected, and stability sheet 154 removed, for those embodiments that have one, the flap portions 168-170 can be separated from one another and the apparatus 100 can be removed without disturbing the medical tube 122. This can occur while a patient is receiving an infusion through the medical tube 122 without stopping the infusion, opening the line, or disturbing the exit site.

Referring now to FIGS. 1-7, in certain embodiments, the enclosure 156 is constructed from a nylon supplex fabric. In some embodiments, the nylon supplex fabric comprises nylon and spandex. In other embodiments, the nylon supplex fabric has nylon and spandex in a range from about 80% nylon to about 20% spandex, from about 90% nylon to about 10% spandex, from about 70% nylon to about 30% spandex, from about 60% nylon to about 40% spandex, from about 50% nylon to about 50% spandex, or a combination thereof.

The material can be a synthetic material, a lycra material, a lycra spandex material, an elastane material, a material comprising polyurethane polymer, polyester polymer, or a combination thereof. In some embodiments, polyurethane polymer is in a range from about 50% to about 95%, from about 60% to about 95%, from about 70% to about 95%, from about 80% to about 95%, from about 85% to about 95%, or a combination there of. In some embodiments, polyurethane polymer is about 50%, about 60%, about 70%, about 80%, about 85%, about 90%, or about 95%.

The enclosure 156 can made from a bonded material or an elastic bonding film. In some embodiments, the bonded material can comprise a fiber web, including a fiber blend comprising from about 50 to about 75 weight percent of a fiber having a fineness less than about 3 denier and from about 25 to about 50 weight percent of a fiber having fineness ranging from about 3 to about 5 denier wherein the fiber web is bound together by fiber bundles transverse to the plane of the web. The fiber blend can further comprise from about 3 to about 7 percent by weight of a fiber having fineness greater than about 5 denier. The fibers comprising the fiber blend can be entirely hydrophobic, or the about 3 to about 5 denier fiber can be hydrophilic.

The absorbent material can exhibit a high degree of absorption and fluid retention and cannot wet back even under compression. The transverse fiber bundles formed during the mechanical bonding of the web can function as wicks for transferring fluid from the surface of the material to the inner portion of the material. The fiber bundles can also act as support structures resisting compression and maintaining void space and absorbent surface area within the material, even when wet. The material can be reusable and can be strong enough to withstand numerous washings. The material can be useful as a component of reusable absorbent products further comprising an outer layer or body-side layer. The outer layer can be fluid impermeable, gas permeable or combinations thereof. In some embodiments, the material can be disposable.

Figure 8:
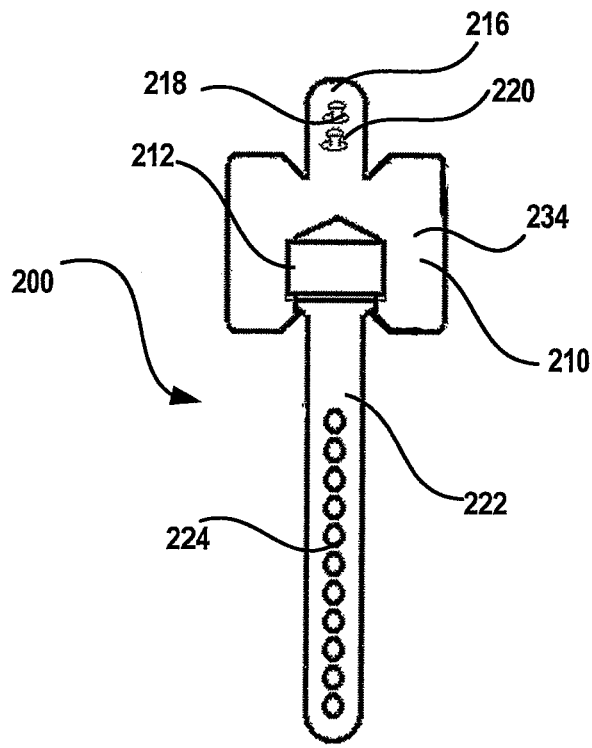
FIG. 8 is a front view of an open detachable fastener in accordance with this disclosure.
Figure 9:
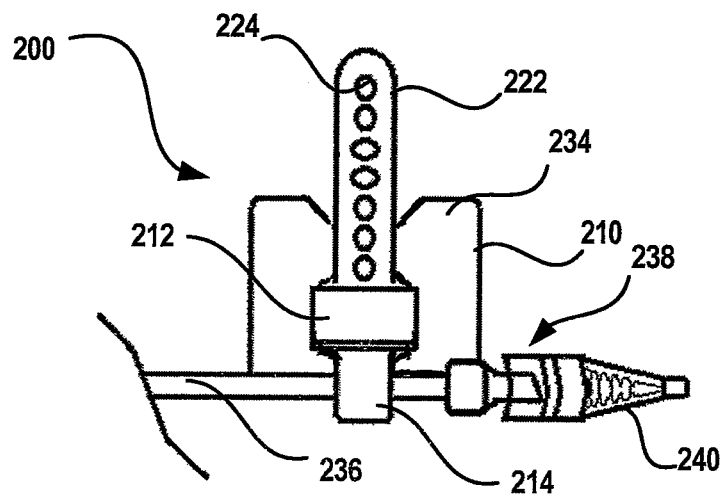
FIG. 9 is a fragmentary front view of a closed detachable fastener holding a medical tube.

Referring now to FIGS. 8-9, an embodiment of a fastener element, generally designated by the numeral 200, is shown. The fastener element 200 is particularly adapted for releasably attaching to a mounting surface, such as the mounting surface 126 shown in FIGS. 1-6. The fastener element 200 is essentially identical to the fastener elements 116 and 128 shown in FIGS. 1-7.

In embodiments, the fastener element 200 includes a base 210, a buckle 212, and an elongated strip 222, that when fed through the buckle 212, can form a recloseable loop 214. The base 210 is a substantially planar member that has a rectangular shape and a tongue 216 housing one or more protruding pins 218, 220. The base 210 is essentially identical to bases 150-152 shown in FIGS. 5-6.

In certain embodiments, the elongated strip 222, having a plurality of holes 224 therein projects downwardly from the base 210 in a direction that is opposite to the tongue 216.

In embodiments, the buckle 212 is a tubular, rectangular structure that projects away from an upper surface 234 of the base 210 in a transverse direction. The loop 214 is formed from the elongated strip 222 by rolling the elongated strip 222 into a circular configuration, inserting the strip into the buckle 212 and engaging pins 218-220 into two of the holes 224.

In embodiments, the loop 214 can be formed around a portion of a medical tube 236 to form a tubular member or tube holder that is essentially the same as the fasteners 116, 128 shown in FIGS. 5-6, that hold the medical tube 236 in place. The loop 214 and the buckle 212 can be aligned in such a manner as to hold the medical tube 236 in a fixed relation with respect to the mounting surface 126 shown in FIGS. 1-6. In some embodiments, a central axis of the medical tube 236 is essentially parallel to the base upper surface 234. In certain embodiments, the medical tube 236 is part of a medical tube assembly 238, which is essentially identical to the medical tube assembly 110 shown in FIG. 6. The loop 214 holds the portion of the medical tube 236, which is adjacent to a connector 240. In certain embodiments, two or more fasteners are used to hold the medical tube 236 safely.

Referring to FIGS. 1-9, the apparatus 100 can include additional components that can increase the stretch, elasticity, or a combination thereof of the substrate 114. In some embodiments, the additional component is optional. In some embodiments, the additional component can be an elastic strip. In further embodiments, the first end or the second end of the body can comprise the elastic strip. In some embodiments, the elastic strip can be layered between a first and a second material.

In an alternative embodiment, the enclosure 156 can include one or more slits located inside the outer perimeter. The one or more slits can vary in dimension and are configured and sized to allow for the passage of varies lengths of catheters and tubes.

In other alternative embodiments, the apparatus 100 can further comprise a support structure (not shown) having an outer perimeter. In some embodiments, the outer perimeter of the support structure comprises surface fasteners.

Some embodiments can include temperature sensors, pulse sensors, or combinations thereof. In some embodiments, the sensor can measure the body temperature of a subject. In further embodiments, the sensor can measure the pulse of a subject. In further embodiments, the sensors can collect information relating to respirations, which is another indicator of sepsis.

In yet another alternative embodiment, the enclosure 156 can be made from a bonded material, having bonded seams, or a combination thereof can reduce the bulk of the enclosure 156. In some embodiments, the enclosure 156 can be made from a bonded material, having bonded seams, or a combination thereof can provide a more streamlined body. In some embodiments, the enclosure 156, when made from a bonded material having bonded seams or a combination thereof can reduce the amount of chafing. In some embodiments, the enclosure 156 made from a bonded material, having bonded seams, or a combination thereof can provide more comfort to wear.

Surprisingly and unexpectedly, the enclosure 156, when made from a bonded material, having bonded seams, or a combination thereof, provided the same or improved catheter line or trachea tube stability when compared to a enclosure 156 made from a non-bonded material, having stitched seams, or a combination thereof. The enclosure 156 made from a bonded material, having bonded seams, or a combination thereof provided the same or improved catheter line or trachea tube stability despite being lighter (e.g. less bulky) compared to a heavier (e.g. more bulky) body made from a non-bonded material, having stitched seams, or a combination thereof.

Some embodiments are suitable for securing a tunneled central catheter. Other embodiments can be used with peritoneal dialysis catheters. These embodiments eliminate damage to the catheter from accidental line and tubing pulls, minimize patient access to the device thereby preventing contamination and infection, lessen skin irritation from medical adhesives, and normalize the medical device, leading to less frequent hospitalization and better quality of life.

Some embodiments can come in sizes that can range from 15" to 34" chest for a central line wrap and trach vest. Other embodiments can come in sizes that range from 15" to 45" waist. Those of skill in the art, however will recognize that sizing depends on the size of the patient.

Figure 10:
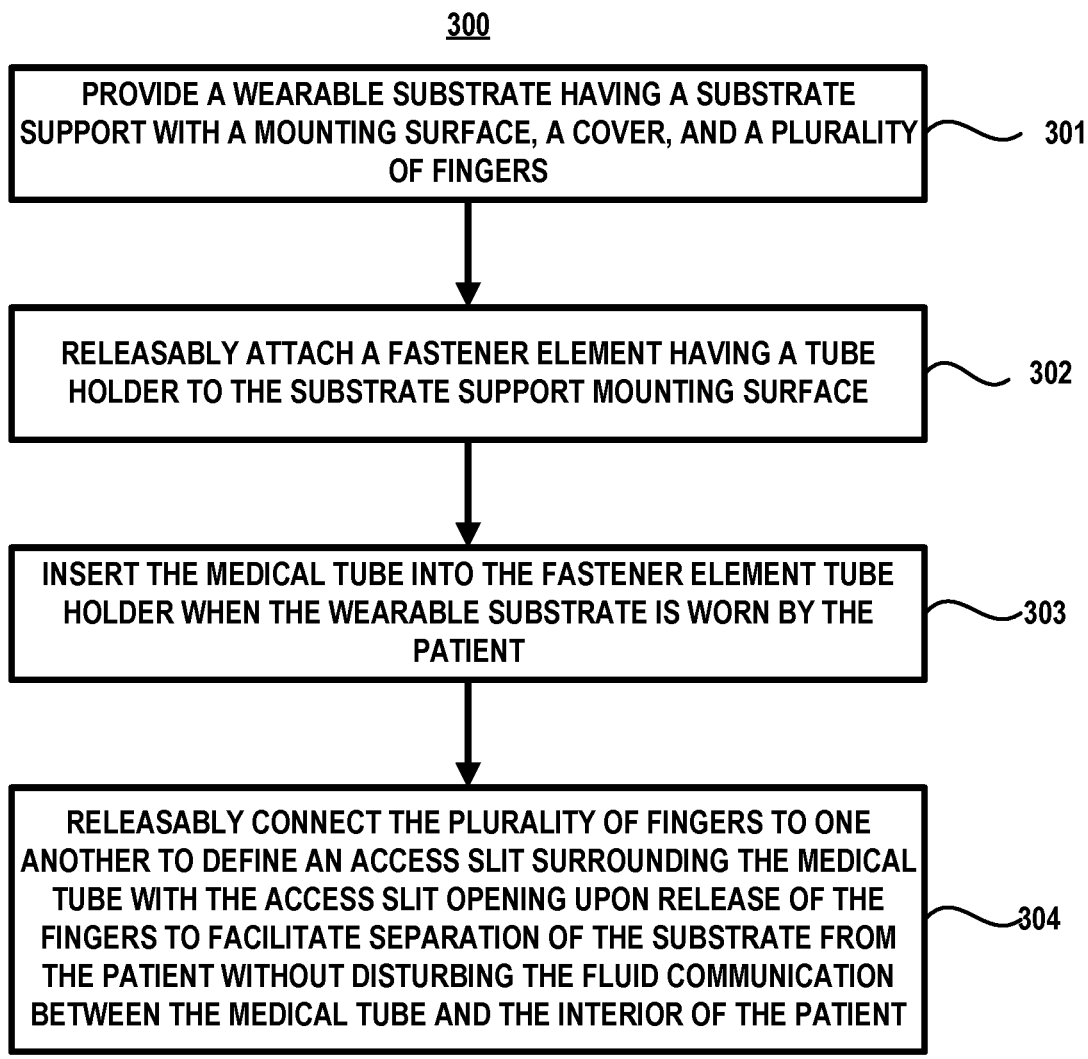
FIG. 10 is a diagram of an exemplary process for installing the apparatus on a user.

Referring to FIG. 10 with continuing reference to the foregoing figures, a method 300 is shown for securing a medical tube assembly having a medical tube that is in fluid communication with the interior of a patient at an insertion point. In certain embodiments, the medical tube assembly can be the medical tube assembly 110 shown in FIGS. 5-7. The method can be practiced with the apparatus 100 shown in FIGS. 1-7 and/or utilizing the fastener element shown in FIGS. 8-9.

The method 300, when implemented, provides the ability to remove the apparatus 100 without disturbing a central line, such as medical tube 122 shown in FIGS. 5-7, that has been inserted into a patient. The apparatus 100 can be removed while a patient is receiving an infusion through a medical tube without stopping the infusion, opening the line, or disturbing the exit site.

At 301, a wearable substrate having a substrate support with a mounting surface, a cover, and a plurality of fingers is provided. In certain embodiments, the substrate can be the substrate 114 shown in FIGS. 1-6, the mounting surface can be the mounting surface 126 shown in FIG. 3, and the cover can be the cover portion 120 shown in FIGS. 1-7. In certain embodiments, the fastener elements can be the fastener element 116 or 128 shown in FIGS. 5-6 and/or the fastener element 200 shown in FIGS. 8-9.

At 302, a fastener element having a tube holder is releasably attached to the substrate support mounting surface. In certain embodiments, the fastener element can be the fastener element 116 or 128 shown in FIGS. 5-6 and/or the fastener element 200 shown in FIGS. 8-9.

At 303, the medical tube is inserted into the fastener element tube holder when the wearable substrate is worn by the patient. In certain embodiments, the medical tube can be the medical tube 122 shown in FIGS. 5-6 and/or the medical tube 236 shown in FIG. 9.

At 304, the plurality of fingers are releasably connected to one another to define an access slit surrounding the medical tube with the access slit opening upon release of the fingers to facilitate separation of the substrate from the patient without disturbing the fluid communication between the medical tube and the interior of the patient. In such embodiments, the flap portions 168-170 can be separated from one another without disturbing the medical tube 122.

Although the invention has been described in considerable detail with reference to certain preferred embodiments thereof, other versions are possible. Therefore, the spirit and scope of the invention will not be limited to the description and the preferred versions contained within this specification.

What is claimed is:

1. A wearable apparatus for securing a medical tube in a tug-resistant manner, the tube having fluid communication with an interior of a patient via an insertion point, the apparatus comprising:
 a support portion having a first edge and a second edge, the support portion having mounting surface thereon;
 a cover portion that releasably attaches to the support portion to define an inner chamber; one or a plurality of opposing finger pairs formed by adjacent fingers within the support portion, the adjacent fingers defining at least one access channel, extending from the first edge toward the second edge, for releaseably receiving and holding the medical tube therethrough; and at least two fastener elements disposed on the mounting surface, wherein the at least two fastener elements are disposed a distance apart on the mounting surface in a location that is displaced from the insertion point, the at least two fastener elements including a first fastener element positioned on one side of the access channel and a second fastener element positioned on an opposite side of the access channel, the first and second faster elements releasably securing a portion of the medical tube to the apparatus;

whereby the apparatus provides protection against dislodgement of the medical tube at the insertion point.

2. The apparatus of claim 1, wherein the one or a plurality of opposing finger pairs are formed as bilateral finger pairs extending from a noncentral location on the support portion to a central location where they meet.

3. The apparatus of claim 2, wherein each opposing finger pair is releasably connected at the central location.

4. The apparatus of claim 1, further comprising a stability sheet releasably attached to the support portion and sandwiched between the one or a plurality of opposing finger pairs and the at least two fastener elements.

5. The apparatus of claim 1, wherein the cover portion is integral with the support portion with the cover portion folding over the support portion to enclose the mounting surface and the at least two fastener elements therein.

6. The apparatus of claim 1, wherein the at least two fastener elements comprise a strap that can form a recloseable loop.

7. The apparatus of claim 1, wherein the at least two fastener elements comprise an elongated strip and a buckle wherein the elongated strip cooperates with the buckle to form a recloseable loop, the elongated strip adapted to cooperate with the buckle in a plurality of locations to snugly accommodate medical tubes of a plurality of diameters.

8. The apparatus of claim 1, wherein the cover is attached to the mounting surface with a hook and loop fastening device.

9. The apparatus of claim 1, further comprising a pair of adjustable shoulder straps attached to the support portion.

10. The apparatus of claim 1, wherein the at least two fastener elements are disposed on the mounting surface in locations that cause the medical tube to be oriented substantially horizontally in an area of the at least two fastener elements.

11. A method for releasably securing a medical tube that is in fluid communication with an interior of a patient at an insertion point, the method comprising:

providing a wearable apparatus to be worn by the patient having a support portion with a mounting surface, the support portion having a first edge and a second edge, a cover portion releasably attachable to the support portion, and one or a plurality of opposing finger pairs formed within the support portion, the opposing finger pairs defining an access channel extending from the first edge toward the second edge, the support portion further having at least two fastener elements releasably disposed a distance apart on the mounting surface and including a first fastener element positioned on one side of the access channel and a second fastener element positioned on an opposite side of the access channel, the first and second fastener elements positioned; in a location that is displaced from the insertion point;

inserting the medical tube into the access channel and into the at least two fastener elements when the wearable apparatus is worn by the patient, and releasably connecting each of the one or a plurality of opposing finger pairs to one another to capture the medical tube within the access channel;

whereupon release of the fingers will facilitate separation of the apparatus from the patient and the medical tube without disturbing the fluid communication between the medical tube and the interior of the patient;

whereby the apparatus prevents dislodgement of the medical tube from the insertion point.

12. The method of claim 11, further comprising closing the cover portion to enclose the access channel, the at least two fastener elements, and at least a portion of the medical tube in a chamber.

13. The method of claim 11, wherein the cover portion and the support portion are integral, the method further comprising folding the cover portion over the support portion to enclose the access channel, the at least two fastener elements, and at least a portion of the medical tube therein.

14. The method of claim 11, further comprising fortifying the support portion with a stability sheet and the at least two fastener elements are releasably disposed on the stability sheet.

15. The method of claim 11, wherein each of the least two fastener elements having a recloseable loop to facilitate insertion of the medical tube therein.

16. The method of claim 15, wherein the at least two fastener elements further comprise a substantially flat elongated strip extending from each fastener, the strip having a free end and a strip engagement apparatus, the method further comprising rolling the substantially flat elongated strip and inserting the free end into the strip engagement apparatus to form the adjustable and recloseable loop.

17. A wearable assembly for releasably securing a medical tube that is in fluid communication with an interior of a patient at an insertion point, the wearable assembly comprising:

a tubular enclosure configured to be worn on the patient, the tubular enclosure having a support portion with a mounting surface, a first edge, a second edge, and a cover portion extending from the second edge configured to releasably attach to the support portion, at least at the first edge, to define an inner chamber, the support portion forming an access channel extending from the first edge toward the second edge for releasably permitting access of the medical tube through the support portion;

at least two openable fastener elements disposed a distance apart on the mounting surface in a location that is displaced from the insertion point, the at least two openable fastener elements including a first fastener element positioned on one side of the access channel and a second fastener element positioned on an opposite side of the access channel, the first and second fastener elements releasably securing the medical tube to the support portion in a way that causes the medical tube to substantially curve before reaching the first fastener element;

whereby the wearable assembly provides improved protection against dislodgement of the medical tube from the insertion point.

* * * * *